US00PP13509P2

(12) United States Plant Patent
Carruth

(10) Patent No.: US PP13,509 P2
(45) Date of Patent: Jan. 28, 2003

(54) FLORIBUNDA ROSE PLANT NAMED 'WEKVOSUIMP'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/995,014

(22) Filed: Nov. 27, 2001

(51) Int. Cl.[7] ..... A01H 5/00
(52) U.S. Cl. ..... Plt./148
(58) Field of Search ..... Plt./148

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Floribunda rose suitable for garden decoration, having flowers of shrimp pink coloration.

1 Drawing Sheet

BOTANICAL CLASSIFICATION

*Rosa hybrida.*

VARIETY DENOMINATION

'WEKvosuimp'.

BACKGROUND OF THE INVENTION

This invention relates to a new and distinct variety of Floribunda Rose. The varietal denomination of the new variety is 'WEKvosuimp'. It has as its seed parent an undisseminated seedling of my creation and as its pollen parent the variety known as 'JACdew' (U.S. Plant Pat. No. 5,122).

SUMMARY OF THE INVENTION

Among the features which distinguish the new variety from other presently available and commercial rose cultivars known to the inventor are the following combination of characteristics: its stipitate glands on the new shoots, the bud surface and the hip surface; its numerous prickles of varying sizes on the major stem, the branches and the new shoots; its rough peduncule and rachis and its large unique ruffled shrimp pink flowers. The plant has a rounded bushy growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKvosuimp' may be asexually propagated by cuttings, budding and grafting.

COMPARISON WITH PARENTS

The new rose may be distinguished from its seed parent, an undisseminated seedling of my creation by the following combination of characteristics: whereas 'WEKvosuimp' bears large (about 7.1 to about 10.6 cm. in diameter) double (about 26 to about 30 petals) flowers of shrimp pink coloration, the seed parent bears significantly smaller (about 3.8 to about 5.3 cm. in diameter) semi-double (about 9 to about 14 petals) flowers of yellow coloration edged with red. The seed parent has a spreading climbing habit with glossy foliage whereas the new variety has a rounded bushy growing habit with moderately semi-glossy foliage.

The new variety may be distinguished from its pollen parent, 'JACdew' by the following combination of characteristics: whereas 'WEKvosuimp' bears large (about 7.1 to about 10.6 cm. in diameter) double (about 26 to about 30 petals) flowers of shrimp pink coloration, the pollen parent bears significantly smaller semi-double flowers of orange red coloration. The pollen parent has an upright habit whereas the new variety has a rounded bushy growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety sometimes bears its flowers singly, sometimes in clusters of three or more per stem. Flowers are borne in somewhat regular rounded to slightly flat clusters on strong medium length stems (about 32 to about 67 cm.). Outdoors, the plant blooms abundantly and nearly continuously during the growing season. The flowers have a slight tea fragrance.

BUD

The peduncle is about 3.1 to about 5.5 cm. in length, of average caliper (about 0.2 to about 0.4 cm. in diameter), and usually erect. It is moderately rough, with numerous stipitate glands and some small prickles. Peduncle color is between 144A and 137B sometimes lightly suffused, especially on the side exposed to the sun, with between 183C and 187D.

Before the calyx breaks, the bud is about 1.2 to about 1.7 cm. in diameter at the widest point, about 1.2 to about 2.1 cm. in length, and pointed to slightly ovoid in shape with a somewhat conspicuous hypanthium. The surface of the bud bears some foliaceous appendages and numerous stipitate glands, usually with slender foliaceous parts extending beyond the tip of the bud about ¼ or more of its length. Bud color is between 144A and 137B.

The sepals are about 1.7 to about 3.3 cm. in length and about 0.7 to about 1.1 cm. in width at the widest point. The outer surface color of the sepal is between 144A and 137B. The inner surface color of the sepal is between 148C and 139D and covered with fine wooly tomentum; sepal margins are lined with numerous stipitate glands and hairs.

As the petals open (after the calyx breaks), the bud is about 1.4 to about 2.1 cm. in diameter at the widest point, about 1.9 to about 2.7 cm. in length, and ovoid to somewhat pointed in form. The color of the under surfaces of the newly opened petals is between 35B and 37A. At the point where the petal attaches, there is a moderately large zone of between 13A and 14B. At the point where the petal attaches, on the upper surface of the newly opened petals, there is a large zone of between 13A and 14B that gradually suffuses to as dark as between 33C and 35B.

BLOOM

When fully open, the bloom ranges from about 7.1 to about 10.6 cm. in diameter. Petalage is double with about 26 to 30 petals and about 1 to 3 petaloids irregularly arranged. When partially open, the bloom form is moderately cupped to somewhat high centered, and the petals are somewhat spiraled to cupped with petal edges somewhat reflexed outward. When fully open, the bloom form is more cupped to somewhat flat, and the petals are more loosely cupped to moderately undulated with petal edges moderately reflexed outward.

PETALS

The substance of the petals is average and of medium thickness, with upper surfaces slightly satiny to somewhat shiny and under surfaces matte to slightly shiny. The outer petals are very broadly obovate to nearly round in shape with mostly rounded apices, sometimes slightly notched to irregularly crenate. The inner petals are broadly obovate to somewhat rounded in shape with irregular apices. The petals are about 3.6 to about 4.7 cm. in length and about 3.6 to about 5.1 cm. in width at the widest point. Petal margins are nearly entire to irregularly crenate.

NEWLY OPENED FLOWER

The under surface of the outer petals is between 48D and 37B. The under surface of the intermediate and inner petals is between 35C and 37B. At the point where the petal attaches, there is a moderately small zone of between 9B and 7C.

On the upper surface of the outer petals, at the point where the petal attaches, there is a moderately large zone of between 9B and 7C that gradually suffuses to as dark as between 38C and 36A. On the upper surfaces of the intermediate and inner petals, at the point where the petal attaches, there is a moderately large zone of between 9B and 7C that gradually suffuses to as dark as between 37B and 37C.

The general tonality of the newly opened flower is between 38C and 36A for the outermost petals and between 38B and 37B for the intermediate and inner petals.

THREE-DAY-OLD FLOWER

The under surface of the outer and inner petals is between 49B and 54D. At the point where the petal attaches, there is a moderately small zone of between 9C and 7D. On the upper surface of the outer and inner petals, at the point where the petal attaches, there is a moderately large zone of between 9C and 7D that gradually suffuse to as dark as between 49C and 56C.

The general tonality of the three-day-old flower is between 49C and 56C.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 114) and are arranged regularly about the pistils; a few are mixed with petaloids. The filaments are of medium length (about 0.4 to about 0.7 cm.), most with anthers. Filaments are between 20A and 23B in color. The anthers are somewhat small for the class and all open approximately at the same time. Anther color is between 21B and 20A when immature and between 200A and 164C at maturity. Pollen is abundant.

FEMALE REPRODUCTIVE ORGANS

Pistils vary in number (average about 56). The styles are moderately uneven, somewhat long to average in length (about 0.4 to about 1.1 cm.), somewhat heavy to average in caliper, and loosely bunched. Stigma color is between 20B and 22B. Style color is between 1D and 2D usually heavily suffused near the top with near 53B. Ovaries are usually all enclosed in the calyx.

Hips are of somewhat short length (about 1.5 to about 2.0 cm.), moderately globular in form, and between 24A and 28B in color when ripe. The hip surface is somewhat smooth with few stipitate glands and very thick fleshy walls. The sepals are permanent. The seeds are irregularly rounded, smooth in texture, approximately 15 to about 21 per hip, about 0.3 to about 0.5 cm. in diameter at the widest point and between 160C and 162C in color.

FOLIAGE

The compound leaves are usually comprised of three to five or more leaflets and are borne abundantly. The five-leaflet leaves are about 7.4 to about 14.3 cm. in length and about 5.1 to about 10.3 cm. in width at the widest point, moderately leathery in texture, and semi-glossy in finish. The terminal leaflets are about 4.5 to about 6.7 cm. in length and about 2.2 to about 3.9 cm. in width at the widest point, shaped moderately oval to broadly ovate with acute apices and rounded to somewhat acute bases. Their margins are usually simply serrate.

The upper surface color of the mature leaf is between 137B and 139A. The under surface color of the mature leaf is between 147B and 136C. The upper surface color of the young leaf is between 146A and 139B, usually moderately suffused with between 187A and 183B. The suffusion color is heavier toward the margin of the new leaves. The under surface color of the young leaf is between 146C and 144B, sometimes moderately suffused with between 187B and 183B.

The rachis is moderately light in caliper and very rough. The upper side is moderately grooved with numerous stipitate glands on the edges of the grooves. The under side of the rachis is very rough with numerous stipitate glands and some small prickles. The rachis color is between 145A and 144B.

The stipules are about 1.1 to about 1.9 cm. in length and moderately wide (about 0.4 to about 0.9 cm.) with somewhat long straight points that usually turn out at an angle of less than 90 degrees. The stipules color is between 137C and 147B.

The petiole is about 1.1 to about 1.9 cm. in length and about 0.1 to about 0.2 cm in diameter at the widest point. The petiole color is between 137C and 147B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a rounded bushy medium height growing habit (about 70 to about 88 cm. in height and about 70 to about 88 cm. spread at the widest point), with very full branching. It displays moderately vigorous growth and the canes are of medium caliper for the class.

The color of the major stems is between 138B and 146B. They bear several large prickles that are about 0.6 to about 0.9 cm. in length. The large prickles are almost straight angled slightly downwards with a moderately long oval base; prickle color is between 165B and 166C. The major stem bears several prickles of varying smaller sizes with similar shape and coloration.

The color of the branches is between 138A and 137A. They bear several large prickles which are of similar size and shape to the large prickles on the major stems; prickle color is between 160B and 161C. The branches bear numerous prickles of varying sizes with similar shape and coloration.

The color of the new shoots is between 144B and 139C sometimes very lightly suffused with between 187B and 183B. They bear several large prickles which are of similar size and shape to the large prickles on the major stems; prickle color is between 183D and 184D. The shoots bear numerous prickles of varying sizes with similar shape and coloration and several stipitate glands.

I claim:

1. A new and distinct Floribunda rose plant of the variety substantially as described and illustrated herein.

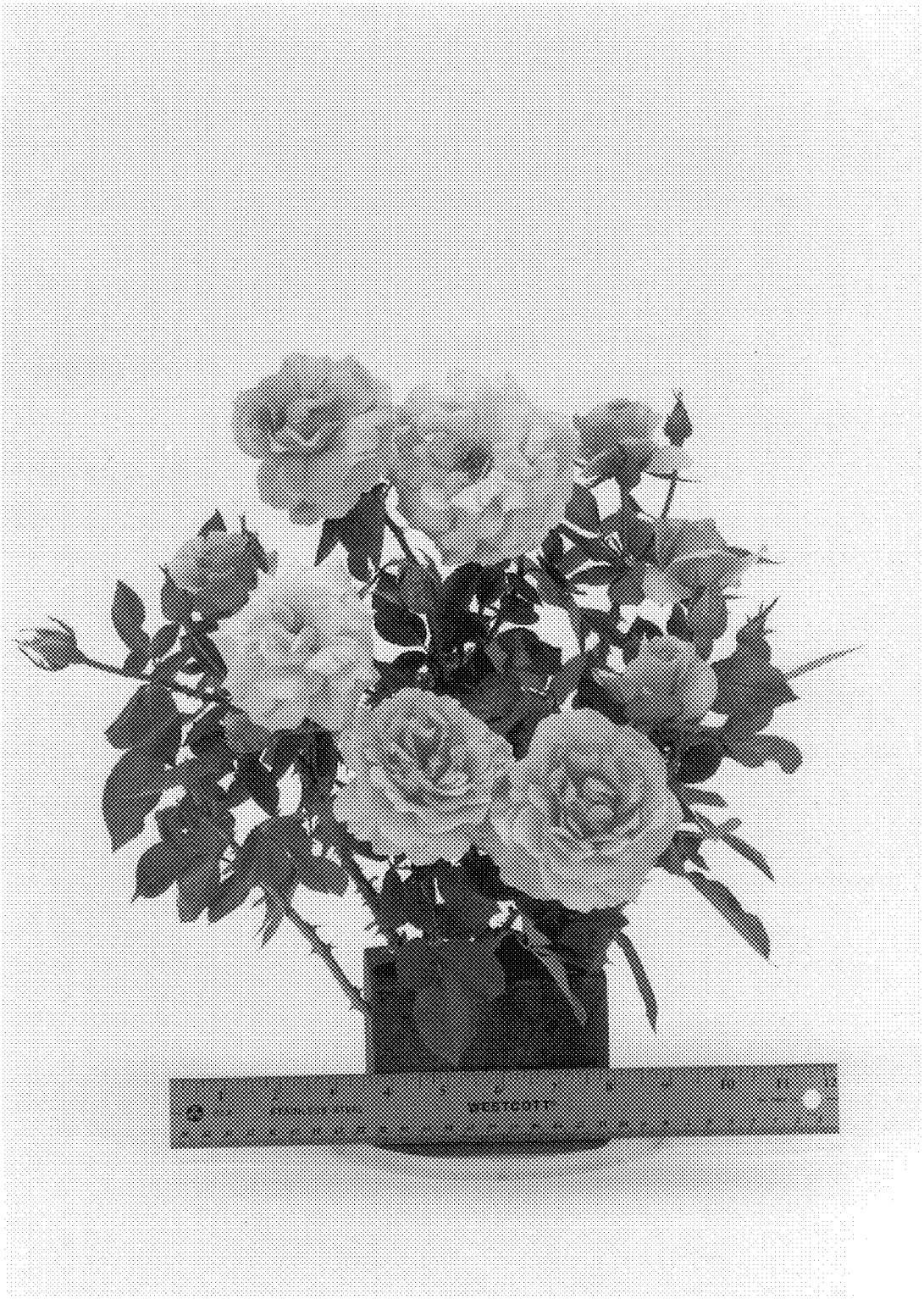

* * * * *